United States Patent
Hamaguchi

(10) Patent No.: US 8,834,363 B2
(45) Date of Patent: Sep. 16, 2014

(54) SLEEP DEPTH DETERMINING DEVICE, SLEEP DEPTH MAINTAINING DEVICE, AND SLEEP DEPTH DETERMINING METHOD

(75) Inventor: Takeshi Hamaguchi, Susono (JP)

(73) Assignee: Toyota Jidosha Kabushiki Kaisha, Toyota-shi (JP)

( * ) Notice: Subject to any disclaimer, the term of this patent is extended or adjusted under 35 U.S.C. 154(b) by 320 days.

(21) Appl. No.: 12/920,478

(22) PCT Filed: Mar. 3, 2010

(86) PCT No.: PCT/JP2010/053439
§ 371 (c)(1),
(2), (4) Date: Sep. 13, 2011

(87) PCT Pub. No.: WO2010/101183
PCT Pub. Date: Sep. 10, 2010

(65) Prior Publication Data
US 2011/0319721 A1  Dec. 29, 2011

(30) Foreign Application Priority Data

Mar. 3, 2009  (JP) ................................. 2009-049383

(51) Int. Cl.
*A61B 5/00* (2006.01)
*A61B 5/0484* (2006.01)
*A61M 21/02* (2006.01)
*A61M 21/00* (2006.01)

(52) U.S. Cl.
CPC ............. *A61B 5/0484* (2013.01); *A61B 5/4812* (2013.01); *A61M 2021/0083* (2013.01); *A61M 2021/0027* (2013.01); *A61M 2230/06* (2013.01); *A61M 2230/65* (2013.01); *A61M 2230/10* (2013.01); *A61M 21/02* (2013.01)
USPC ............................. 600/300; 600/544; 340/575

(58) Field of Classification Search
USPC ........................ 600/300, 544, 545; 340/573.1
See application file for complete search history.

(56) References Cited

U.S. PATENT DOCUMENTS

| 5,507,716 | A |   | 4/1996 | LaBerge et al. |
|---|---|---|---|---|
| 5,595,488 | A | * | 1/1997 | Gozlan et al. ................. 434/236 |
| 7,179,218 | B2 |   | 2/2007 | Raniere |
| 2003/0095476 | A1 |   | 5/2003 | Mollicone et al. |
| 2008/0234785 | A1 |   | 9/2008 | Nakayama et al. |
| 2010/0076273 | A1 |   | 3/2010 | Shigetou |

FOREIGN PATENT DOCUMENTS

| JP | 4347140 A | 12/1992 |
|---|---|---|
| JP | 2002028242 A | 1/2002 |

(Continued)

OTHER PUBLICATIONS

International Preliminary Report on Patentability (Chapter I of the Patent Cooperation Treaty), dated Sep. 22, 2011 (5 pages).

*Primary Examiner* — Charles A Marmor, II
*Assistant Examiner* — Etsub Berhanu
(74) *Attorney, Agent, or Firm* — Gifford, Krass, Sprinkle, Anderson & Citkowski, P.C.

(57) ABSTRACT

A sleep depth determining device 2 is a device for determining an object person M's depth of sleep using a sensitivity threshold which is the minimum stimulus intensity that can be sensed by the object person M in a sleep state and includes: a stimulus giving unit 5 that gives a first stimulus P1 and a second stimulus P2 stronger than the first stimulus P1 to the object person M; a sense detecting unit 6 that detects whether the object person M senses the first stimulus P1 and the second stimulus P2; and a sleep depth determining unit 7 that determines that the object person M's depth of sleep is a depth of sleep S2 corresponding to a sensitivity threshold between a first stimulus intensity T2$a$ and a second stimulus intensity T2$b$ when the sense detecting unit 6 detects that the object person M does not sense the first stimulus P1 but senses the second stimulus P2. Accordingly, it is possible to precisely determine that the object person M's depth of sleep is the depth of sleep S2.

6 Claims, 10 Drawing Sheets

(56) References Cited

FOREIGN PATENT DOCUMENTS

| JP | 2005177158 A | 7/2005 |
|----|--------------|--------|
| JP | 2006026122 A | 2/2006 |
| JP | 2007117608   | 5/2007 |
| JP | 2007244597 A | 9/2007 |
| JP | 2008049067 A | 3/2008 |
| JP | 2008229248 A | 10/2008 |
| JP | 2009213707 A | 9/2009 |

* cited by examiner

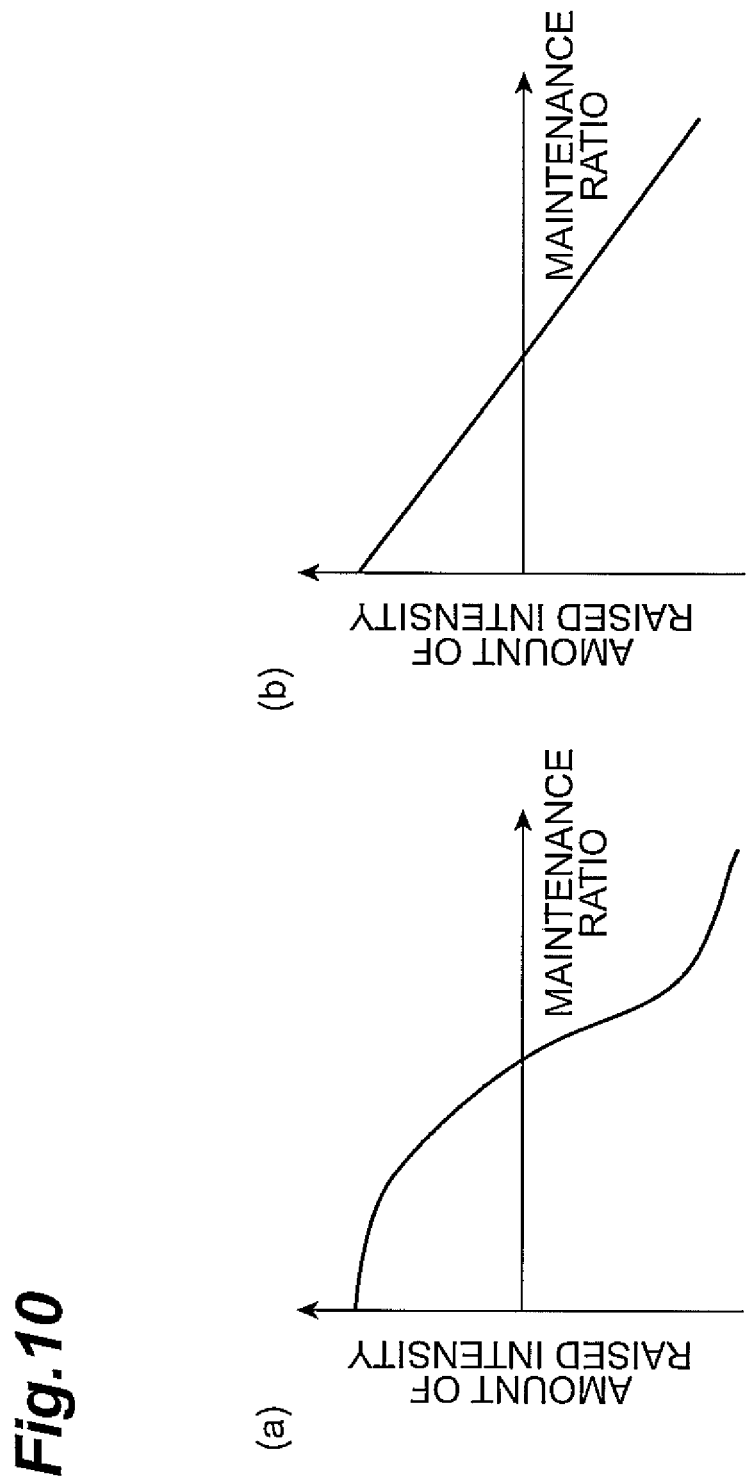

SLEEP DEPTH DETERMINING DEVICE, SLEEP DEPTH MAINTAINING DEVICE, AND SLEEP DEPTH DETERMINING METHOD

CROSS REFERENCE TO RELATED APPLICATIONS

This application is the U.S. national phase of PCT/JP2010/053439 filed Mar. 3, 2010, which claims priority of Japanese Patent Application 2009-049383 filed Mar. 3, 2009, which are incorporated herein by reference.

TECHNICAL FIELD

The present invention relates to a sleep depth determining device, a sleep depth maintaining device, and a sleep depth determining method.

BACKGROUND ART

Conventionally, as a method of precisely determining a sleep state or a sleep pattern including a depth of sleep of an object person, a polysomnography method of comprehensively measuring various waveforms in a variety of biological information such as brain waves, eyeball movement, muscle movement, or electrocardiographs is known. In this polysomnography method, the sleep depth representing a depth of sleep is determined by comprehensively distinguishing the waveforms in the measured biological information, and the sleep state is determined by analyzing the depth of sleep (for example, see Patent Literature 1).

CITATION LIST

Patent Literature

Japanese Unexamined Patent Application Publication No. 2007-244597(JP-A-2007-244597)

SUMMARY OF INVENTION

Technical Problem

In the above-mentioned method of determining a sleep state, it is necessary to detect the biological information such as an object person's brain waves or eyeball movement with a large number of sensors and to analyze the detected signals by the use of complex processes so as to precisely determine the object person's depth of sleep.

The invention is made to solve the above-mentioned problem. An object of the invention is to provide a sleep depth determining device that can precisely determine an object person's depth of sleep with a simple and easy process, a sleep depth maintaining device having the sleep depth determining device, and a sleep depth determining method.

Solution to Problem

To solve the above-mentioned problem, in the course of intensive study, the inventor focused on the sensitive threshold of the human body in a sleep state in relation to a stimulus. The sensitivity threshold represents the minimum stimulus intensity which can be sensed by an object person in a sleep state with a predetermined depth of sleep and varies depending on the depth of sleep. Further observation of the sensitivity threshold revealed that the sensitivity threshold varies depending on the object persons in spite of having the same depth of sleep. Therefore, the inventor found that it is possible to precisely determine the depth of sleep without complexly processing detected signals by studying a stimulus giving technique using an object person's sensitivity threshold, and thus completed the invention.

To accomplish the above-mentioned object, according to an aspect of the invention, there is provided a sleep depth determining device for determining an object person's depth of sleep using a sensitivity threshold which is the minimum stimulus intensity that can be sensed by the object person in a sleep state with a predetermined depth of sleep, including: a stimulus giving unit that gives the object person a first stimulus with a first stimulus intensity and a second stimulus with a second stimulus intensity greater than the first stimulus intensity; a sense detecting unit that detects whether the object person senses the first stimulus and the second stimulus; and a sleep depth determining unit that determines that the object person's depth of sleep is a depth of sleep corresponding to a sensitivity threshold between the first stimulus intensity and the second stimulus intensity when the sense detecting unit detects that the object person does not sense the first stimulus but senses the second stimulus.

According to another aspect of the invention, there is provided a sleep depth determined method of determining an object person's depth of sleep using a sensitivity threshold which is the minimum stimulus intensity that can be sensed by the object person in a sleep state with a predetermined depth of sleep, including: a stimulus giving step of causing a stimulus giving unit to give the object person a first stimulus with a first stimulus intensity and a second stimulus with a second stimulus intensity greater than the first stimulus intensity; a sense detecting step of causing a sense detecting unit to detect whether the object person senses the first stimulus and the second stimulus; and a sleep depth determining step of causing a sleep depth determining unit to determine that the object person's depth of sleep is a depth of sleep corresponding to a sensitivity threshold between the first stimulus intensity and the second stimulus intensity when it is detected in the sense detecting step that the object person does not sense the first stimulus but senses the second stimulus.

In the sleep depth determining device and the sleep depth determining method, when it is detected that the object person does not sense the first stimulus but senses the second stimulus stronger than the first stimulus, it is considered that the sensitivity threshold which is the minimum stimulus intensity that can be sensed by the object person in a sleep state with a predetermined depth of sleep lies between two stimulus intensities of the first and second stimuli and it is thus determined that the object person's depth of sleep is the depth of sleep corresponding to the sensitivity threshold lying between two stimulus intensities. Accordingly, it is possible to determine an object person's depth of sleep with a simple and easy process of giving two stimuli of the first and second stimuli and detecting the object person's sense in relation thereto. The object person's actual sense is detected. Accordingly, even when the sensitivity threshold slightly varies depending on the object persons or an object person's sensitivity threshold slightly varies due to external environments, it is possible to absorb the variations and thus to precisely determine the object person's depth of sleep.

Since the depth of sleep and the sensitivity threshold corresponding to the depth of sleep are set by stages in advance, the stimulus giving unit may give the object person a stimulus with a stimulus intensity smaller than a predetermined sensitivity threshold set in advance to correspond to a predetermined level of depth of sleep as the first stimulus and may give the object person a stimulus with a stimulus intensity greater than the predetermined sensitivity threshold as the second stimulus. Since a predetermined sensitivity threshold and a depth of sleep corresponding thereto are used, it is possible to raise a response speed in determining the depth of sleep. Since the number of times of giving the first and second stimuli to the object person can be reduced, it is possible to reduce the influence of the stimulus on the object person's depth of sleep.

To solve the above-mentioned problem, according to still another aspect of the invention, there is provided a sleep depth maintaining device having the sleep depth determining device and maintaining the object person's depth of sleep at an intermediate level lower than the maximum level, including: a maintenance control unit that determines a condition of a maintenance stimulus to be given to the object person on the basis of the sensitivity threshold in the depth of sleep of the intermediate level so as to maintain the object person's depth of sleep at the intermediate level and causes the stimulus giving unit to give the object person the maintenance stimulus on the basis of the determined condition, after the sleep depth determining unit determines that the object person's depth of sleep is a depth of sleep of the intermediate level.

In the sleep depth maintaining device, after the depth of sleep is precisely determined by the sleep depth determining device, the condition for giving the maintenance stimulus to the object person to maintain the depth of sleep at an intermediate level is determined on the basis of the sensitivity threshold in the intermediate level of depth of sleep. Accordingly, it is possible to precisely maintain the object person's depth of sleep at the intermediate level. In the sleep depth determining device, when a depth of sleep and a sensitivity threshold corresponding to the depth of sleep are set by stages in advance, it is possible to precisely determine the depth of sleep as described above and it is thus possible to maintain the object person's depth of sleep with good responsibility. When they are set by stages, the number of times of giving a stimulus to the object person is reduced as described above. Accordingly, it is possible to reduce a variation in the object person's depth of sleep in relation to a given stimulus and to more easily maintain the object person's depth of sleep.

The maintenance control unit may cause the sense detecting unit to detect whether the object person senses the maintenance stimulus when the maintenance stimulus is given to the object person, and may adjust the condition so as to increase the stimulus intensity of the maintenance stimulus when it is detected that the object person does not sense the maintenance stimulus. In this case, it is possible to continuously maintain the object person's depth of sleep at the intermediate level with a simple and easy process.

In adjustment of the condition, the sleep depth maintaining device may further include a maintenance time calculating unit that calculates a maintenance time when the sense detecting unit detects that the object person senses the maintenance stimulus, and the maintenance control unit may adjust the condition so as to increase the stimulus intensity of the maintenance stimulus in reverse proportion to the length of the maintenance time at the time of raising the stimulus intensity of the maintenance stimulus. The sleep depth maintaining device may further include a maintenance ratio calculating unit that calculates a maintenance ratio which is a ratio of the number of times when the sense detecting unit detects that the object person senses the maintenance stimulus to the number of times when the maintenance stimulus is given to the object person, and the maintenance control unit may adjust the condition so as to increase the stimulus intensity of the maintenance stimulus in reverse proportion to the magnitude of the maintenance ratio at the time of raising the stimulus intensity of the maintenance stimulus. By raising the stimulus intensity of the maintenance stimulus in reverse proportion to the maintenance time or the maintenance ratio, it is possible to prevent the object person from completely waking with the giving of the stimulus with an excessively raised stimulus intensity give when the object person's depth of sleep is slightly deeper than the intermediate level. Accordingly, it is possible to continuously maintain the object person's depth of sleep at the intermediate level.

Advantageous Effects of Invention

In the sleep depth determining device and the sleep depth determining method according to the invention, it is possible to precisely determine an object person's depth of sleep with a simple and easy process. In the sleep depth maintaining device including the sleep depth determining device, it is possible to precisely maintain an object person's depth of sleep.

BRIEF DESCRIPTION OF DRAWINGS

FIG. 10 is a diagram illustrating a relation between a maintenance ratio and an intensity increment in the example shown in FIG. 9.

DESCRIPTION OF EMBODIMENTS

Hereinafter, a sleep depth determining device and a sleep depth maintaining device having the sleep depth determining device according to exemplary embodiments of the invention will be described in detail with reference to the accompanying drawings.

Figure 1:
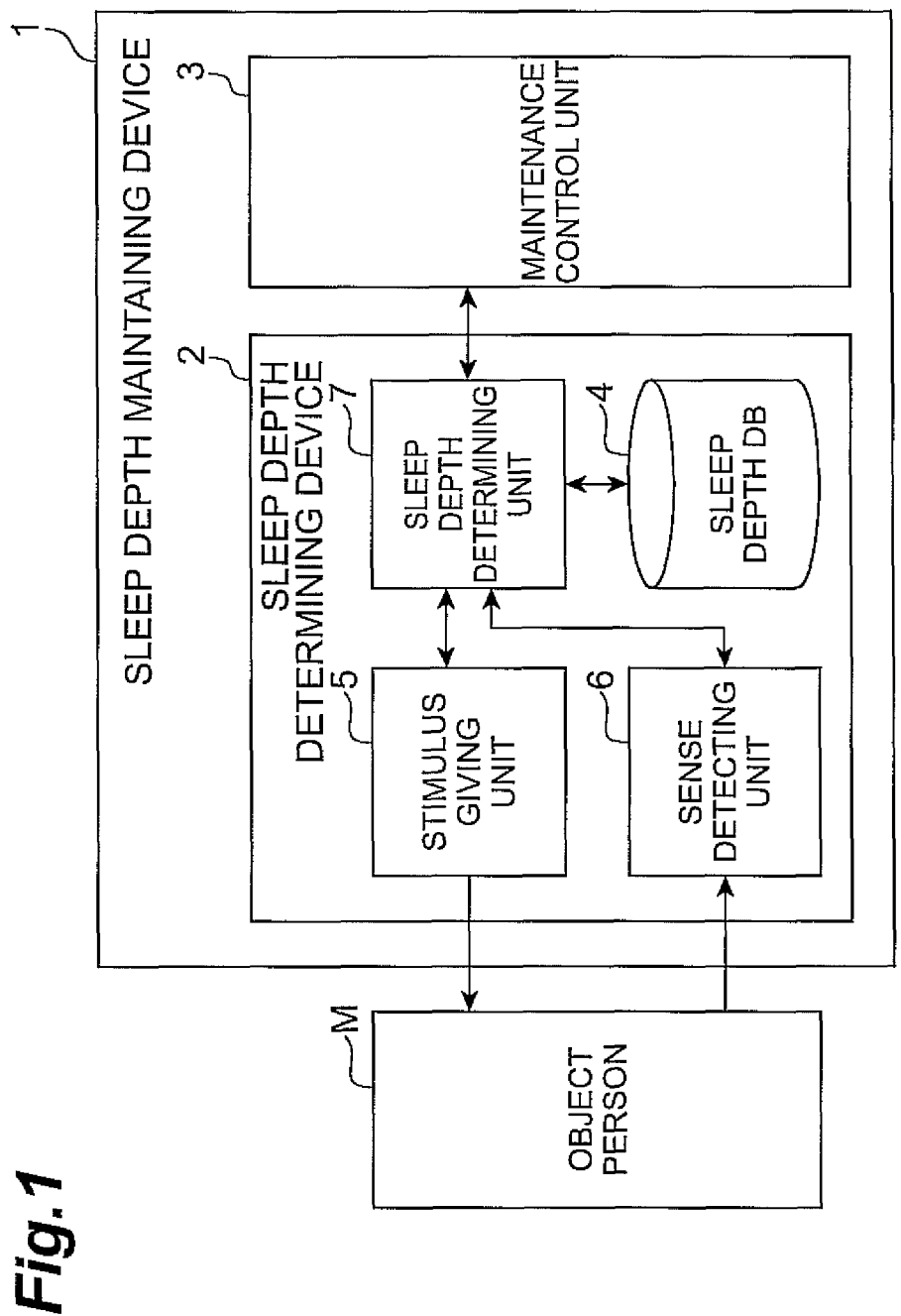
FIG. 1 is a diagram illustrating the configuration of a sleep depth maintaining device according to an exemplary embodiment of the invention.

The sleep depth maintaining device 1 includes a sleep depth determining device 2 and a maintenance control unit 3 as shown in FIG. 1, and is mounted on a vehicle such as an automobile. After an object person M who is a vehicle driver feels sleepy during driving and parks the vehicle, the sleep depth maintaining device 1 determines the object person M's depth of sleep in a sleep state by the use of the sleep depth determining device 2 and maintains the object person M's depth of sleep at a depth of sleep suitable for a light sleep by the use of the maintenance control unit 3.

Figure 2:
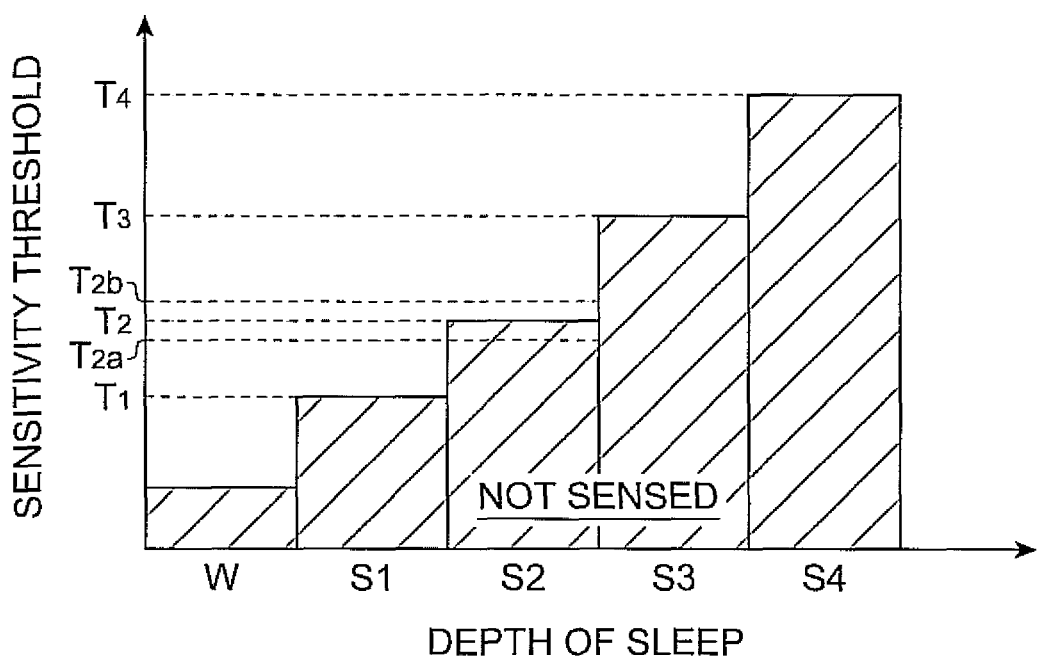
FIG. 2 is a diagram illustrating a relation between a depth of sleep and a sensitivity threshold.

The depth of sleep means levels representing predetermined steps of a depth of sleep and is divided into four steps of S1, S2, S3, and S4 from a level of a shallow sleep to a level of a deep sleep (see FIG. 2). When the object person M's depth of sleep in a sleep state is maintained at a depth of sleep S2 which is an intermediate level lower than the maximum level of depth of sleep S4, for example, it is possible to provide the object person M with a suitable light sleep.

The sleep depth determining device 2 is a device for determining the object person M's depth of sleep using a sensitivity threshold which is the minimum stimulus intensity that can be sensed by the object person M sleeping with a predetermined depth of sleep. The sleep depth determining device 2 outputs the object person M's determined depth of sleep to the maintenance control unit 3. When the determined depth of sleep is not a desired depth of sleep to be maintained (for example, the depth of sleep S2), the maintenance control unit 3 gives a waking stimulus or a sleeping stimulus to the object person M and controls the sleep depth determining device 2 to determine the depth of sleep again.

The sleep depth determining device 2 includes a sleep depth database (hereinafter, referred to as "sleep depth DB") 4, a stimulus giving unit 5, a sense detecting unit 6, and a sleep depth determining unit 7.

The sleep depth DB 4 is a storage unit that stores sensitivity threshold information (see FIG. 2) of each object person M in which depths of sleep S1 to S4 of the object person M in a sleep state and sensitivity thresholds T1 to T4 corresponding to the depths of sleep S1 to S4 are set by stages. The sensitivity threshold information stored in the sleep depth DB 4 is experimentally calculated in advance using a statistical process or the like. The relation between the sensitivity threshold and the depth of sleep shown in FIG. 2 shows that the object person M in a sleep state with the depths of sleep does not sense a stimulus intensity smaller than those of the sensitivity thresholds T1 to T4 ("not sensed" in the drawing) and senses a stimulus intensity equal to or greater than those of the sensitivity thresholds T1 to T4. In FIG. 2, W represents that the object person M wakes up.

The stimulus giving unit 5 is a unit for giving a physical stimulus to the object person M and gives a first stimulus P1 with a first stimulus intensity T2a and a second stimulus P2 with a second stimulus intensity T2b greater than the first stimulus intensity T2a to the object person M. For example, a speaker giving an auditory stimulus using a sound can be used as the stimulus giving unit 5 and the stimulus intensity is changed by adjusting a sound pressure. The speaker is built in, for example, a headrest of a seat.

The first and second stimuli P1 and P2 given by the stimulus giving unit 5 have stimulus intensities with respect to the sensitivity threshold T2 corresponding to the depth of sleep S2 which is a desired depth of sleep to be maintained. As shown in FIG. 2, the first stimulus P1 as one stimulus has a stimulus intensity T2a smaller than the sensitivity threshold T2 and the second stimulus P2 as the other stimulus has a stimulus intensity T2b greater than the sensitivity threshold T2.

When a predetermined start condition is satisfied and the determination of the depth of sleep is started, stimulus instructing information including stimulus intensity information of the first stimulus intensity T2a and the second stimulus intensity T2b based on the sensitivity threshold information stored in the sleep depth DB 4 is input to the stimulus giving unit 5 from the sleep depth determining unit 7. When the stimulus instructing information is input, the stimulus giving unit 5 gives the first stimulus P1 with the first stimulus intensity T2a to the object person M continuously plural times at an interval t, for example, 20 times at an interval of 1 second, on the basis of the stimulus intensity information (see FIG. 3(a)).

After giving the first stimulus P1, the stimulus giving unit 5 gives the second stimulus P2 with the second stimulus intensity T2b to the object person M continuously plural times at an interval t on the basis of the stimulus intensity information, similarly to the first stimulus. At the time of giving a stimulus, the stimulus giving unit 5 first gives a weak stimulus to reduce the influence of the given stimulus on the object person M' sleep state. After giving the first stimulus P1 and after giving the second stimulus P2, the stimulus giving unit 5 outputs end information indicating that the giving of the stimulus is ended to the sleep depth determining unit 7. The stimulus giving unit 5 gives the waking stimulus, the sleeping stimulus, and a maintenance stimulus to be described later to the object person M on the basis of instruction information from the maintenance control unit 3.

Figure 3:
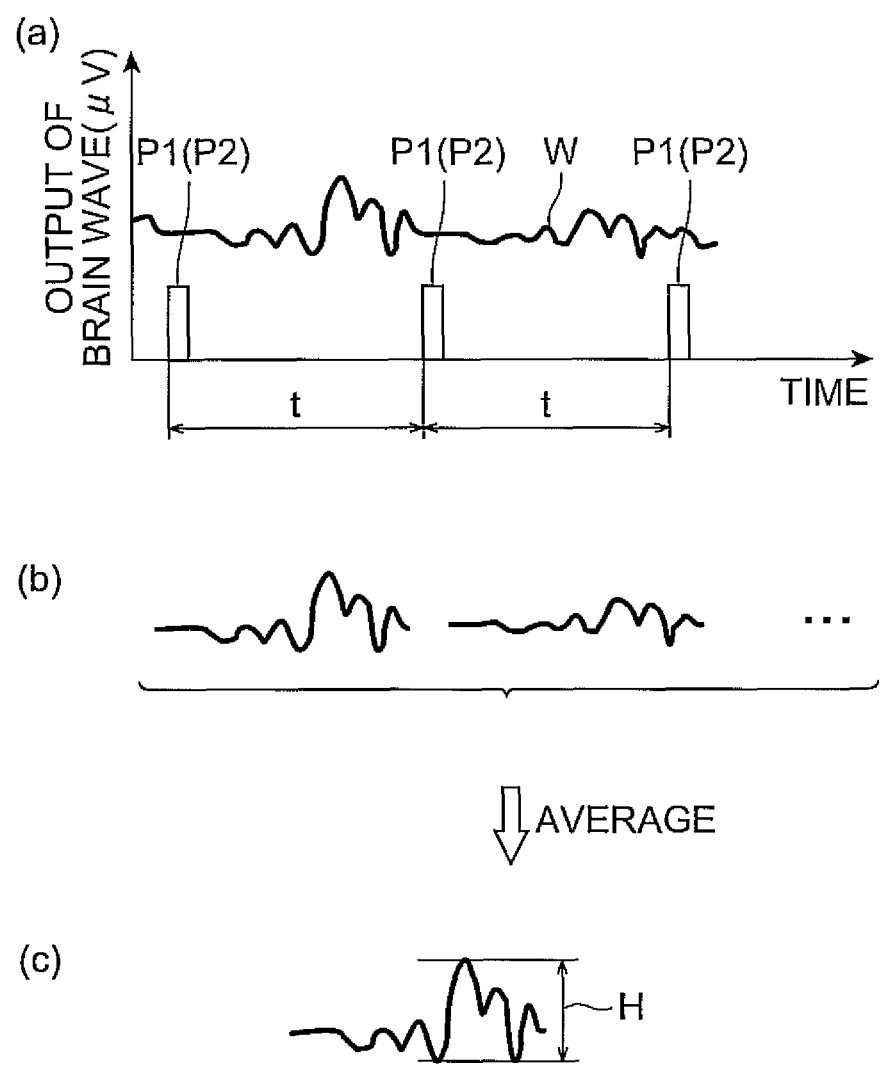
FIG. 3 is a diagram illustrating an example of a sense detecting operation of a sense detecting unit.

The sense detecting unit 6 serves to detect whether the object person M to which the stimulus is given senses the first and second stimulus P1 and P2. For example, an electroencephalograph detecting the object person M's brain waves W is used as the sense detecting unit 6. As shown in FIG. 3(b), the sense detecting unit 6 detects the brain waves W responsive to the stimulus (for example, first stimulus P1) given plural times from the stimulus giving unit 5 as brain wave data and calculates an average thereof as averaged brain wave data (see FIG. 3(c)).

When the amplitude H of the averaged brain wave data is smaller than a predetermined threshold, the sense detecting unit 6 detects that the object person M does not sense the given stimulus. When the amplitude H of the averaged brain wave data is equal to or greater than the predetermined threshold, the sense detecting unit 6 detects that the object person M senses the given stimulus. The sense detecting unit 6 outputs sensing information indicating the detection results to the sleep depth determining unit 7. The sense detecting unit 6 also detects the object person M's sensing the maintenance stimulus given from the stimulus giving unit 5 on the basis of the instruction information from the maintenance control unit 3.

The sleep depth determining unit 7 serves to determine that the object person M's depth of sleep is the depth of sleep S2 corresponding to the sensitivity threshold T2 between the first stimulus intensity T2a and the second stimulus intensity T2b when the sense detecting unit 6 detects that the object person M does not sense the first stimulus P1 but senses the second stimulus P2. As described above, when a predetermined start condition is satisfied and the determination of the depth of sleep is started, the sleep depth determining unit 7 accesses the sleep depth DB 4, generates the stimulus instructing information including the stimulus intensity information of the first stimulus intensity T2a and the second stimulus intensity T2b on the basis of the threshold information stored therein, and outputs the generated stimulus instructing information to the stimulus giving unit 5.

When end signals indicating that the giving of the first and second stimuli P1 and P2 are input from the stimulus giving unit 5 and sensing information indicating the sensing of the first and second stimuli P1 and P2 is input from the sense detecting unit 6 after outputting the stimulus instructing information, the sleep depth determining unit 7 determines the object person M's depth of sleep. Specifically, the sleep depth determining unit 7 determines that the object person M's depth of sleep is the depth of sleep S2, when the sense detecting unit 6 detects that the object person M does not sense the first stimulus P1 but senses the second stimulus P2.

When the sense detecting unit 6 detects that the object person M senses both of the first and second stimuli P1 and p2, the sleep depth determining unit 7 determines that the object person M's depth of sleep is a depth of sleep (for example, the depth of sleep S1) shallower than the depth of sleep S2. When it is detected that the object person M does not sense any of the first and second stimuli P1 and P2, the sleep depth determining unit 7 determines that the object person M's depth of sleep is a depth of sleep (for example, the depth of sleep S3) deeper than the depth of sleep S2. The sleep depth determining unit 7 outputs the determination result on the depth of sleep to the maintenance control unit 3.

The maintenance control unit 3 serves to make a maintenance control so as to maintain the object person M's depth of sleep at the depth of sleep S2 within a time predetermined as a light sleep time after the sleep depth determining unit 7 determines that the object person M's depth of sleep is the depth of sleep S2 which is an intermediate level. After the sleep depth determining unit 7 determines that the object person M's depth of sleep is the depth of sleep S2, the maintenance control unit 3 determines a condition for giving a maintenance stimulus (for example, a stimulus slightly stronger than the sensitivity threshold in the depth of sleep S2 is intermittently given) on the basis of the sensitivity threshold in the depth of sleep S2, and intermittently gives the maintenance stimulus P3 to the object person M at a predetermined interval t on the basis of the determined condition by the use of the stimulus giving unit 5 (see FIG. 4(a)). By giving the maintenance stimulus P3 based on the sensitivity threshold, the object person M's depth of sleep in a sleep state is maintained at the depth of sleep S2 and the transfer to the depths of sleep S3 and S4 deeper than the depth of sleep S2 is suppressed within a predetermined range.

Figure 4:
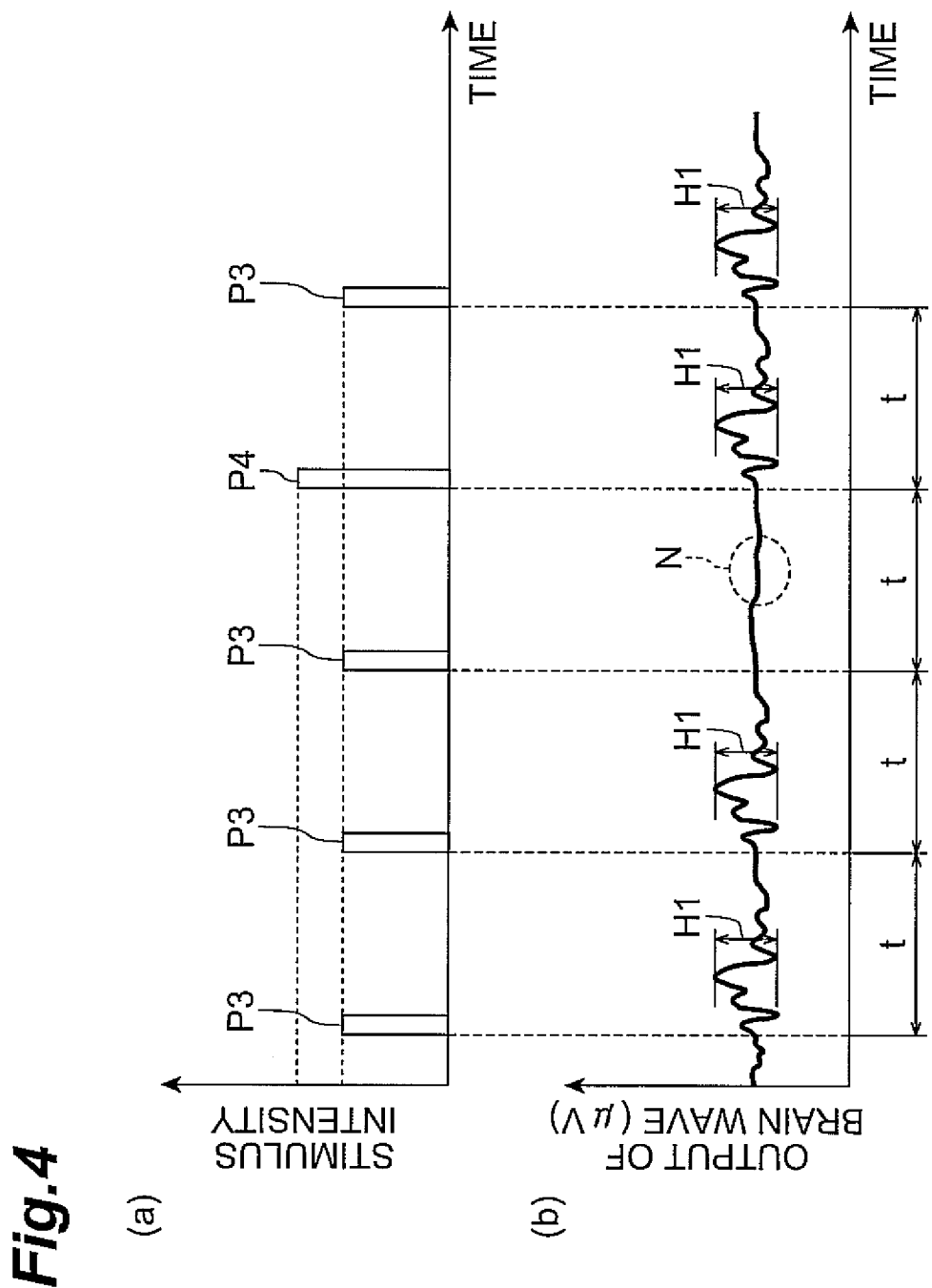
FIG. 4 is a diagram illustrating an example of a stimulus given by a maintenance control unit.

The maintenance control unit 3 controls the sense detecting unit 6 to detect whether the object person M senses the maintenance stimulus P3 when it is given to the object person M (see FIG. 4(b)). When the amplitude H1 of the object person M' brain wave data (not averaged) is equal to or greater than a predetermined threshold, the sense detecting unit 6 detects that the object person M senses the maintenance stimulus P3. On the other hand, when the amplitude H1 of the object person's brain wave data (not averaged) is smaller than the predetermined threshold (for example, in case of the brain wave W indicated by region N in FIG. 4(b)), the sense detecting unit 6 detects that the object person M does not sense the maintenance stimulus P3. Since the averaging process of the sleep depth determining device 2 is not performed to detect the sense but the detected brain wave data is used without any change, the response speed of the sense detection is raised.

When the sense detecting unit 6 detects that the object person M does not sense the maintenance stimulus P3 after the object person M's depth of sleep is determined as the depth of sleep S2 and the maintenance control is started, the maintenance control unit 3 determines that the object person M's depth of sleep is deeper than the depth of sleep S2. When it is determined that the object person M's depth of sleep is deepened, the maintenance control unit 3 adjusts the condition so as to raise the stimulus intensity of the maintenance stimulus P3 given to the object person M to the depth of sleep P4 to shallow the object person M's depth of sleep. For example, a method of calculating an increment depending on the object person M's sleep state before the depth of sleep is deepened and adjusting the condition can be used as the method of adjusting the condition. The maintenance control unit 3 controls the stimulus giving unit 5 to give the maintenance stimulus P4 based on the adjusted condition to the object person M.

When the maintenance stimulus P4 based on the adjusted condition is given to the object person M, the maintenance control unit 3 continuously controls the sense detecting unit 6 to detect whether object person M senses the stimulus. When it is detected that the object person M senses the maintenance stimulus P4 based on the adjusted condition, the maintenance control unit 3 performs a process of lowering the stimulus intensity of the maintenance stimulus P4 to the maintenance stimulus P3 and returning the condition to the not-adjusted condition. On the other hand, when it is detected that the object person M does not sense the maintenance stimulus P4 based on the adjusted condition, the maintenance control unit 3 re-adjusts the condition so as to further raise the stimulus intensity of the maintenance stimulus P4 and repeatedly raises the stimulus intensity until the object person M senses the stimulus.

The maintenance control unit 3 makes the above-mentioned maintenance control until a predetermined light sleep time passes. When the light sleep time passes, the maintenance control unit 3 gives a strong waking stimulus for awaking the object person M at once, awakes the object person M from the light sleep, and ends the process.

Figure 5:
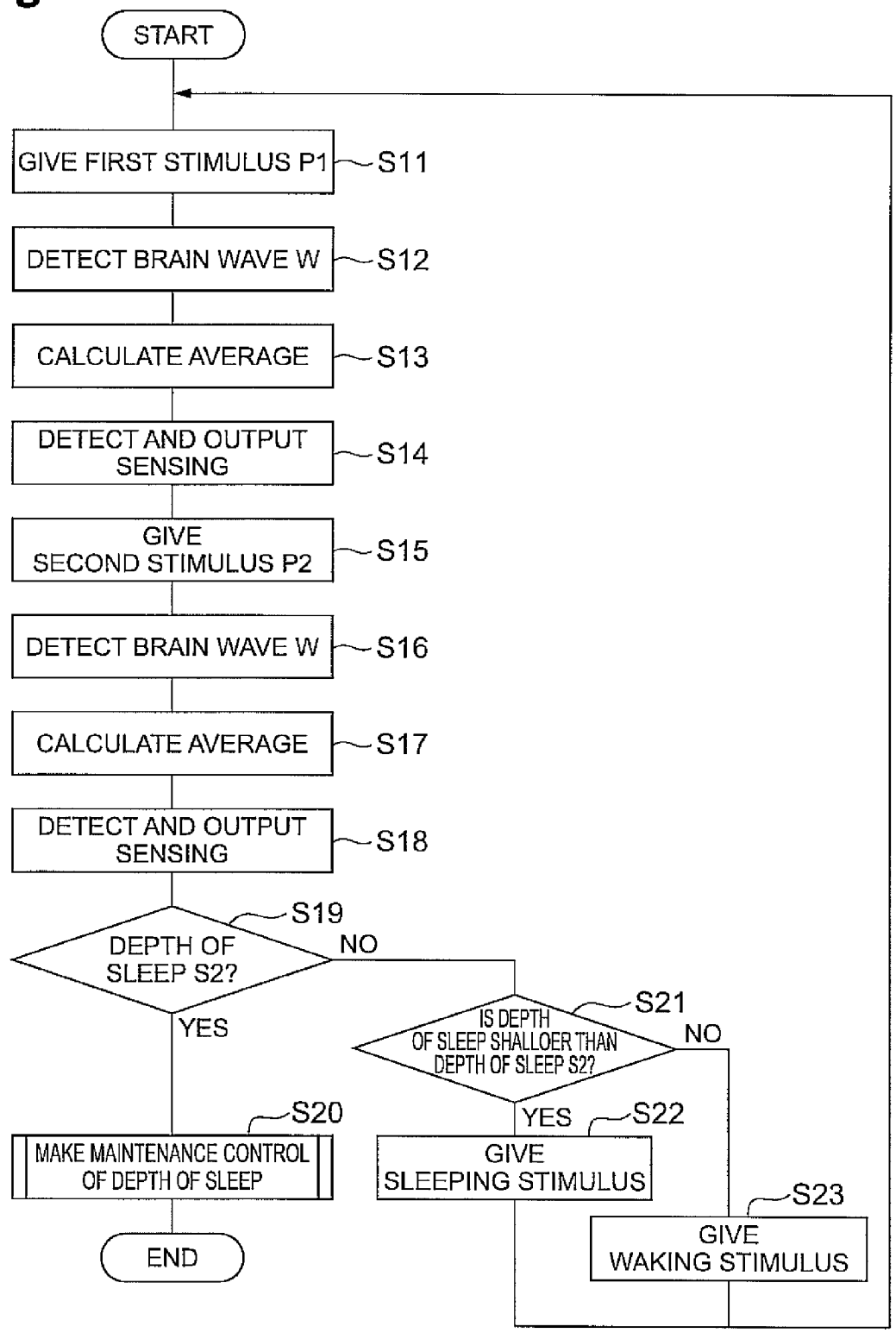
FIG. 5 is a flowchart illustrating a flow of operations of the sleep depth maintaining device shown in FIG. 1.
Figure 6:
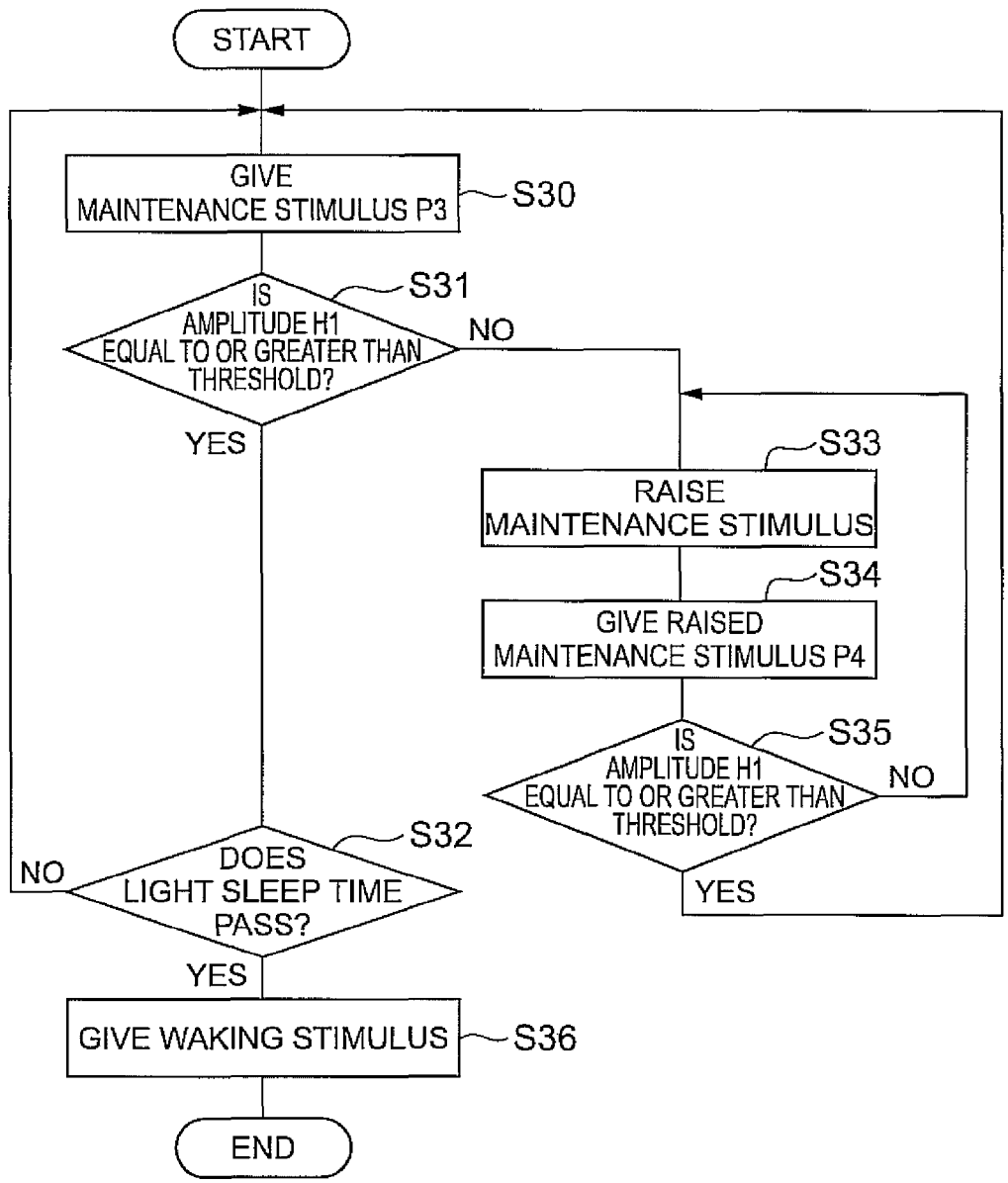
FIG. 6 is a flow chart illustrating a flow of operations of controlling maintenance of a depth of sleep.

Then, the flow of operations of the sleep depth maintaining device 1 will be described with reference to the flowchart shown in FIGS. 5 and 6. A series of control processes described below are repeatedly performed with a predetermined period.

First, the stimulus giving unit 5 gives the first stimulus P1 to the object person M continuously plural times at a predetermined interval (S11). When the first stimulus P1 is continuously given to the object person M in step S11, the sense detecting unit 6 detects the brain waves W of the object person M (S12), averages the brain waves, and outputs the averaged brain wave data (S13). The sense detecting unit 6 compares the amplitude H of the averaged brain wave data with a predetermined threshold, detects "sensed" when the amplitude H is equal to or greater than the predetermined threshold, detects "not sensed" when the amplitude H is smaller than the predetermined threshold, and outputs the detection result to the sleep depth determining unit 7 as the sensing information indicating the sensing of the first stimulus P1 (S14).

Subsequently, when the stimulus giving unit 5 gives the second stimulus P2 stronger than the first stimulus P1 to the object person M continuously plural times at a predetermined interval (S15), the sense detecting unit 6 detects the brain waves W of the object person M, calculates the averaged brain wave data, and outputs the sensing information indicating the sensing of the second stimulus P2 (S15 to S18), similarly to the case where the first stimulus P1 is given.

When the sensing information on the giving of the first and second stimuli P1 and P2 is input from the stimulus giving unit 5, the sleep depth determining unit 7 determines whether the object person M's depth of sleep is the depth of sleep S2 corresponding to the sensitivity threshold between the first and second stimuli P1 and P2 on the basis of the input sensing information (S19). At the time of determining whether the measured depth of sleep is the depth of sleep S2, when the sensing information states that the object person M does not sense the first stimulus P1 but senses the second stimulus P2, the sleep depth determining unit 7 determines that the object person M's depth of sleep is the depth of sleep S2.

When it is determined in step S19 that the object person's depth of sleep is the depth of sleep S2, the process of step 20 is performed. That is, the maintenance control of the depth of sleep S2 is performed for the predetermined light sleep time (S20).

On the other hand, when it is determined in step S19 that the object person M's depth of sleep is not the depth of sleep S2, the sleep depth determining unit 7 determines whether the object person M's depth of sleep is shallower than the depth of sleep S2 on the basis of the sensing information on the giving of the first and second stimuli P1 and P2 in step S21. When it is determined that the object person M's depth of sleep is shallower than the depth of sleep S2, the maintenance control unit 3 gives a sleeping stimulus to the object person M to deepen the object person M's depth of sleep (S22). When the object person M's depth of sleep is deeper than the depth of sleep S2, the maintenance control unit gives a waking stimulus to the object person M to shallow the object person M's depth of sleep (S23). Thereafter, the process of step S11 is repeatedly performed again.

The maintenance control of the depth of sleep will be described in detail with reference to FIG. 6. The maintenance control described below is repeatedly performed with a predetermined period.

When the maintenance control of the depth of sleep S2 is started, the maintenance control unit 3 controls the stimulus giving unit 5 to give the maintenance stimulus P3 to the object person M on the basis of the condition for giving the maintenance stimulus (S30). In this condition, the maintenance stimulus P3 given in step S30 is the maintenance stimulus based on the sensitivity threshold in the depth of sleep S2. When the maintenance stimulus P3 is given in step S30, the maintenance control unit 3 controls the sense detecting unit 6 to detect the brain wave data of the object person M's brain waves W in response to the maintenance stimulus P3 to the sense detecting unit 6 without averaging the brain wave data and to detect whether the amplitude H1 thereof is equal to or greater than a predetermined threshold (S31).

When it is detected in step S31 that the amplitude H1 of the brain wave data is equal to or greater than a predetermined threshold, the maintenance control unit 3 controls the stimulus giving unit 5 to continuously give the maintenance stimulus until a predetermined light sleep time passes (S30 to S32). On the other hand, when the amplitude H1 of the brain wave data is smaller than the predetermined threshold, the maintenance control unit 3 adjusts the condition so as to raise the stimulus intensity of the maintenance stimulus in step S33.

After adjusting the condition so as to raise the stimulus intensity of the maintenance stimulus in step S33 (S33), the maintenance control unit 3 controls the stimulus giving unit 5 to give the maintenance stimulus P4 with the raised stimulus intensity to the object person M on the basis of the adjusted condition (S34). When the maintenance stimulus P4 with the raised stimulus intensity is given in step S34, the maintenance control unit 3 controls the sense detecting unit 6 to calculate the brain wave data of the object person M in response to the maintenance stimulus P4 and to detect whether the amplitude H1 is equal to or greater than a predetermined threshold (S35), similarly to step S31.

When it is detected in step S35 that the amplitude H1 of the brain wave data is equal to or greater than the predetermined threshold, the maintenance control unit 3 controls the stimulus giving unit 5 to continuously give the maintenance stimulus P3 in step S1 again until the predetermined light sleep time passes (S30 to S32). On the other hand, when the amplitude H1 of the brain wave data is smaller than the predetermined threshold, the maintenance control unit 3 raises the stimulus intensity of the maintenance stimulus again and repeatedly performs the same process until the amplitude H1 of the brain wave data is equal to or greater than the predetermined threshold in step S33. The maintenance control unit 3 repeatedly makes the above-mentioned maintenance control, gives a strong waking stimulus for awaking the object person M at once (S36) when the light sleep time passes, to awake the object person M from the light sleep state, and then ends the flow of operations.

In the sleep depth determining device 2 according to this embodiment, when it is detected that the object person M does not sense the first stimulus P1 but the object person M senses the second stimulus P2 stronger than the first stimulus P1, it is considered that the sensitivity threshold which is the minimum stimulus intensity that can be sensed by the object person M in a sleep state lies between two stimulus intensities T2a and T2b of the first and second stimuli P1 and P2 and it is thus determined that the object person M's depth of sleep is the depth of sleep S2 corresponding to the sensitivity threshold T2 lying between two stimulus intensities T2a and T2b. Accordingly, it is possible to determine an object person M's depth of sleep with a simple and easy process of giving two stimuli of the first and second stimuli P1 and P2 and detecting the object person's sense in relation thereto. The object person M's actual sense is detected. Accordingly, even when the sensitivity threshold slightly varies depending on the object persons M or an object person M's sensitivity threshold slightly varies due to external environments, it is possible to absorb the variations by finely changing the stimulus intensities of the first and second stimuli P1 and P2 and thus to precisely determine the object person M's depth of sleep.

Since the depth of sleep and the sensitivity threshold corresponding to the depth of sleep are set by stages in advance in the sleep depth DB 4, the stimulus giving unit 5 may give the object person a stimulus with a stimulus intensity smaller than a predetermined sensitivity threshold set in advance to correspond to a predetermined level of depth of sleep (for example, the depth of sleep S2) as the first stimulus P1 and may give the object person a stimulus with a stimulus intensity greater than the predetermined sensitivity threshold as the second stimulus P2. Since a predetermined sensitivity threshold and a depth of sleep corresponding thereto are used in the sleep depth determining device 2 according to this embodiment, it is possible to raise a response speed in determining the depth of sleep. Since the number of times of giving the first and second stimuli P1 and P2 to the object person M can be reduced, it is possible to reduce the influence of the stimulus on the object person M's depth of sleep.

In the sleep depth maintaining device 1 according to this embodiment, after the depth of sleep is precisely determined by the sleep depth determining device 2, the condition for giving the maintenance stimulus P3 to the object person M to maintain the depth of sleep at an intermediate level of depth of sleep S2 is determined on the basis of the sensitivity threshold in the depth of sleep S2. Accordingly, it is possible to precisely maintain the object person M's depth of sleep at the depth of sleep S2. In the sleep depth determining device 2, since a depth of sleep and a sensitivity threshold corresponding to the depth of sleep are set by stages in advance, it is possible to precisely determine the depth of sleep as described above and it is thus possible to maintain the object person M's depth of sleep with good responsibility. When they are set by stages, the number of times of giving a stimulus to the object person M is reduced as described above. Accordingly, it is possible to reduce a variation (for example, waking) in the object person M's depth of sleep in relation to a given stimulus and to more easily maintain the object person M's depth of sleep.

The maintenance control unit 3 causes the sense detecting unit 6 to detect whether the object person M senses the maintenance stimulus when the maintenance stimulus is given to the object person M, and adjusts the condition so as to increase the stimulus intensity of the maintenance stimulus P3 when it is detected that the object person M does not sense the maintenance stimulus P3. Accordingly, it is possible to continuously maintain the object person M's depth of sleep at the depth of sleep S2 with a simple and easy process.

The above-mentioned embodiment describes an example of the sleep depth determining device 2 or the sleep depth maintaining device 1 according to the invention. The sleep depth determining device 2 or the sleep depth maintaining device 1 according to the invention is not limited to the example, but the devices according to the embodiment may be modified or may be applied to apparatuses other than the vehicle without departing from the scope of the appended claims. For example, although it is stated in the embodiment that the sensing of the object person M is determined on the basis of the brain waves W by the use of the sense detecting unit 6 determines, a level of a skin potential or a variation in heart beat may be detected and the sensing of the object person M may be determined on the basis of the detection result. When the level of a skin potential or the variation in heart beat is used in determination, it is possible to precisely determine the depth of sleep without performing the averaging process.

Although the term, depth of sleep, is used to express the level of the depth of sleep in the embodiment, a term, sleep stage, which is an international indicator, may be used to express the depth of sleep.

Although it is stated in the embodiment that the stimuli with stimulus intensities based on the sensitivity threshold T2 corresponding to the depth of sleep S2 which is a desired depth of sleep to be maintained are used as the first and second stimuli P1 and P2 given by the stimulus giving unit 5, stimuli with small stimulus intensities that cannot be sensed by the object person M with the depth of sleep S1 may be given as the first and second stimuli to the object person M and then the stimulus intensities of the first and second stimuli to be given may be slowly raised. In this case, by determining the sensing of the object person in response to the first and second stimuli several times on the basis of the gradual sensitivity thresholds, it is possible to determine the object person M's depth of sleep.

Figure 7:
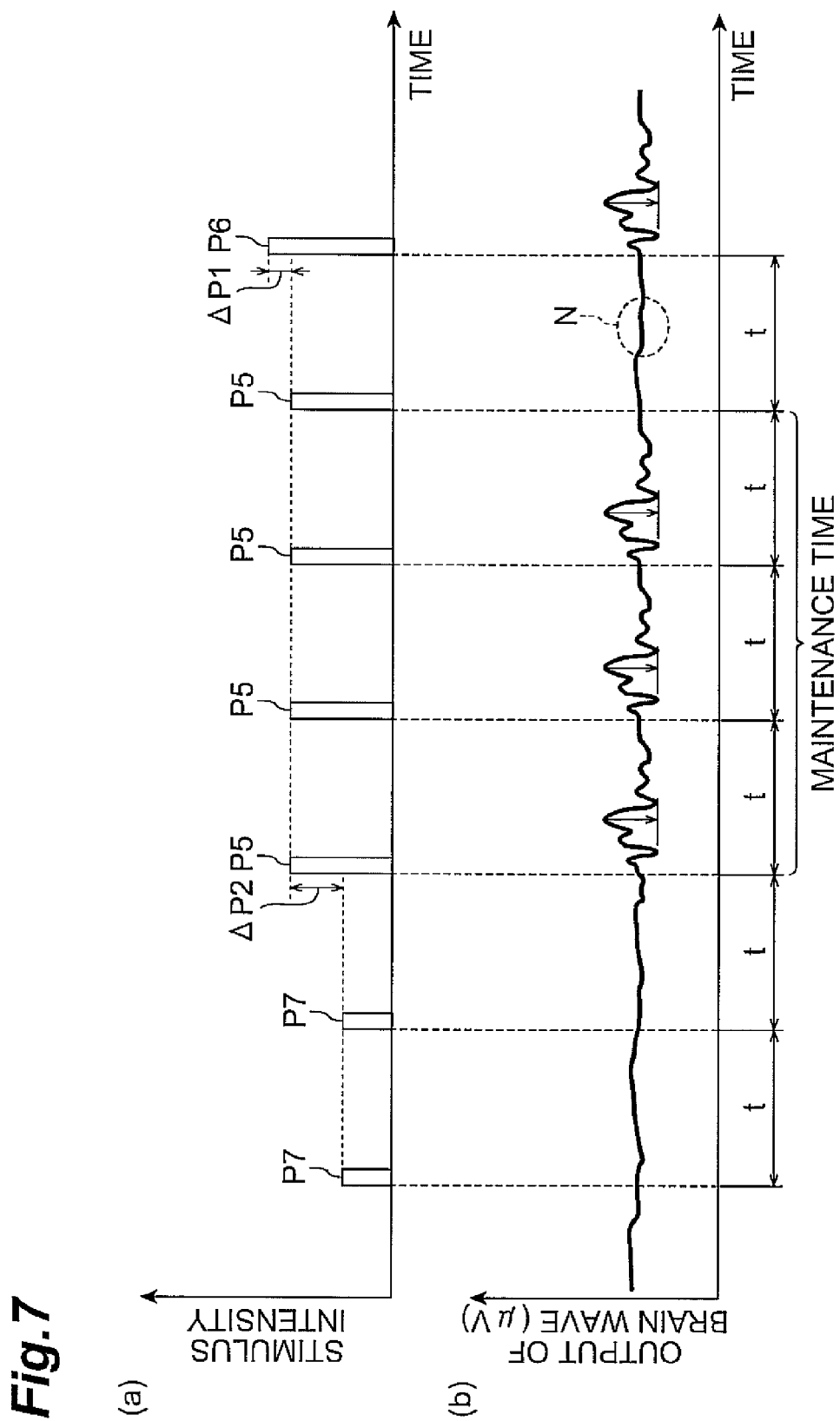
FIG. 7 is a diagram illustrating an example of a stimulus adjusting operation of the maintenance control unit.
Figure 8:
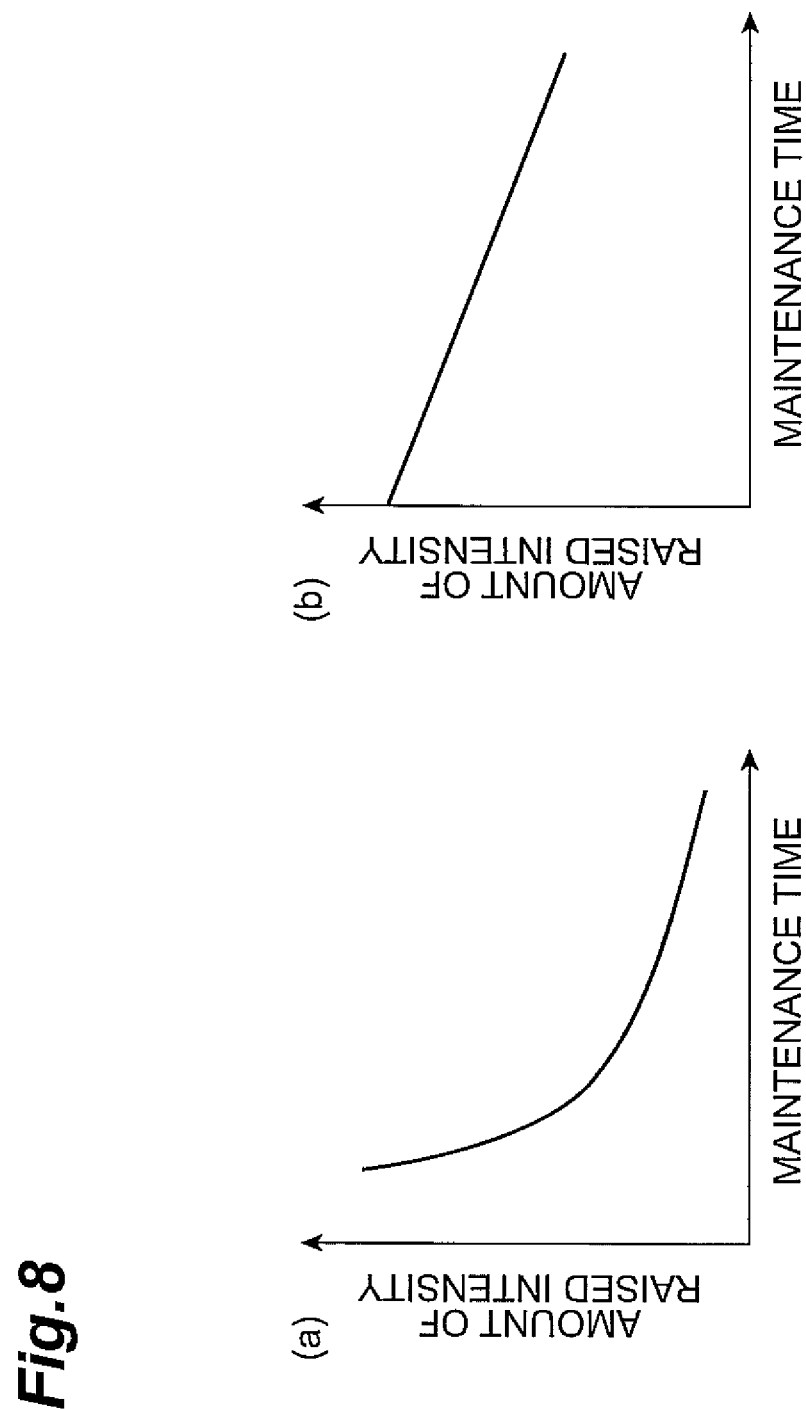
FIG. 8 is a diagram illustrating a relation between a maintenance time and an intensity increment in the example shown in FIG. 7.

In the embodiment, when the maintenance control unit 3 adjusts the condition to raise the stimulus intensity of the maintenance stimulus P3 to be given to the object person M so as to shallow the object person M's depth of sleep, the increment is calculated depending on the object person M's sleep state before the depth of sleep is deepened. However, for example, the sleep depth maintaining device 1 may further include a maintenance time calculating unit that calculates a maintenance time when the sense detecting unit 6 detects that the object person M senses the maintenance stimulus, and the maintenance control unit 3 may adjust the condition to raise the stimulus intensity of the maintenance stimulus P5 by a predetermined amount $\Delta P1$ into a maintenance stimulus P6 in reverse proportion to the length of the maintenance time of the object person M before the depth of sleep is deepened, as shown in FIG. 7, when the object person M does not sense the maintenance stimulus P5 (the brain wave W indicated by region N) and the stimulus intensity of the maintenance stimulus P5 is raised. In this case, since the stimulus intensity is raised in reverse proportion to the length of the maintenance time, the raised amount $\Delta P1$ of the stimulus intensity from the maintenance stimulus P5 to the maintenance stimulus P6 is smaller than the raised amount $\Delta P2$ of the stimulus intensity from a maintenance stimulus P7 to a maintenance stimulus P5 when there is no maintenance time. Regarding the relation between the maintenance time and the intensity raising amount in reverse proportion to each other, the raised amount may decrease like a quadric function with respect to the maintenance time as shown in FIG. 8(a), or the raised amount may decrease like a linear function with respect to the maintenance time as shown in FIG. 8(b).

Figure 9:
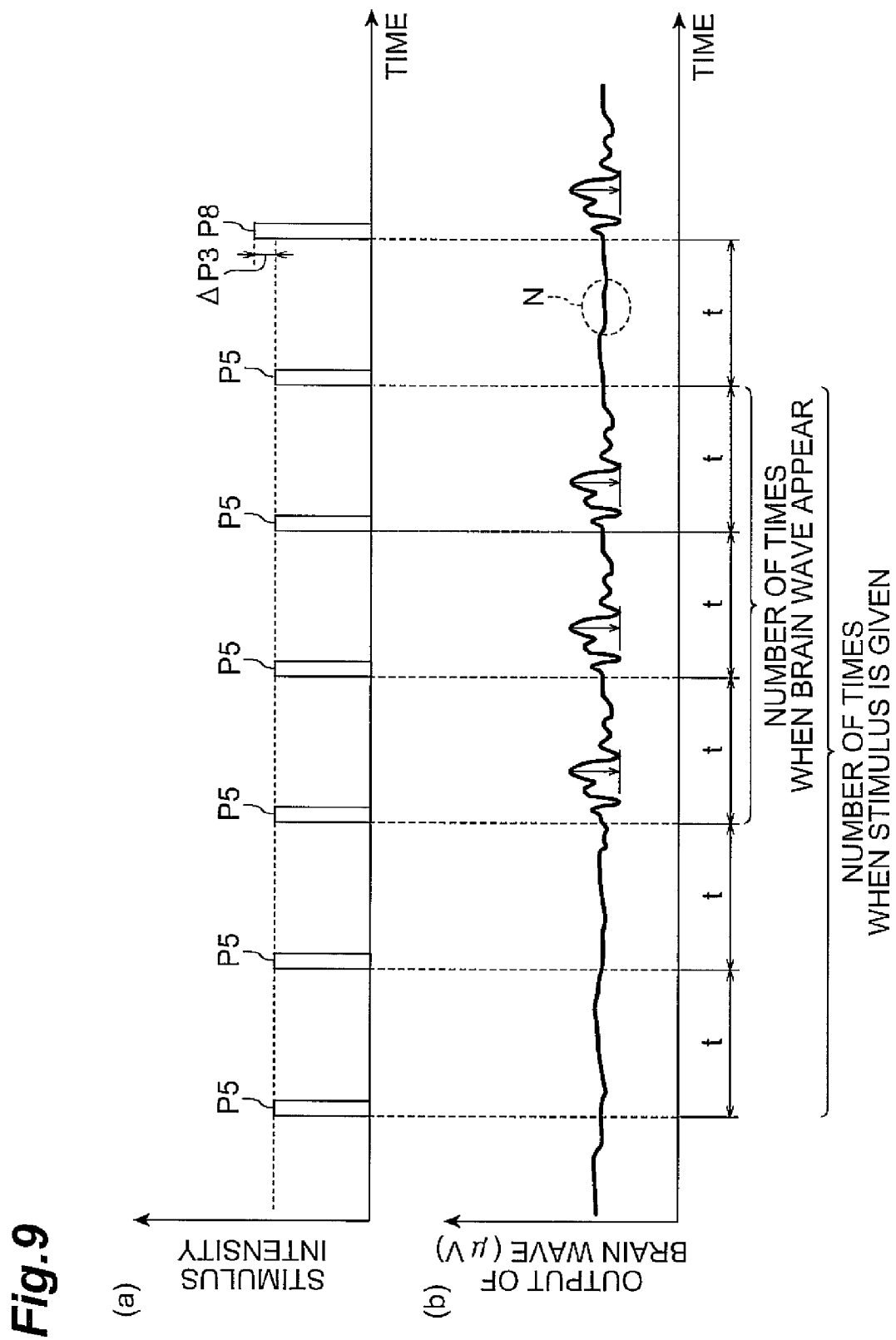
FIG. 9 is a diagram illustrating another example of the stimulus adjusting operation of the maintenance control unit.

The sleep depth maintaining device 1 may further include a maintenance ratio calculating unit that calculates a maintenance ratio which is a ratio of the number of times (the number of times when the brain wave appears) when the sense detecting unit 6 detects that the object person M senses the maintenance stimulus to the number of times when the maintenance stimulus is given to the object person M, and the maintenance control unit 3 may adjust the condition so as to raise the stimulus intensity of the maintenance stimulus P5 by a predetermined amount $\Delta P3$ to the maintenance stimulus P8 in reverse proportion to the magnitude of the maintenance ratio at the time of raising the stimulus intensity P5 of the maintenance stimulus, as shown in FIG. 9. Regarding the relation between the maintenance time and the intensity raising amount, the raised amount may decrease like a sigmoid function as shown in FIG. 10(a), or the raised amount may decrease like a linear function with respect to the maintenance time as shown in FIG. 10(b). In this way, by raising the stimulus intensity of the maintenance stimulus in reverse proportion to the maintenance time or the maintenance ratio, it is possible to prevent the object person M from completely waking with the giving of the stimulus with an excessively raised stimulus intensity given when the object person M's depth of sleep is slightly deeper than the depth of sleep S2 of an intermediate level. Accordingly, it is possible to continuously maintain the object person M's depth of sleep at the depth of sleep S2. The condition may be adjusted by changing factors such as a stimulus interval, a stimulus time, or a duty ratio of giving of a stimulus other than the stimulus intensity at the time of adjusting the condition.

Although it is stated in the above-mentioned embodiment that the sleep depth maintaining device 1 is applied to a vehicle, the sleep depth maintaining device 1 according to the invention may be applied to a bed or an easy chair other than the vehicle, whereby it is used for refresh in a normal life or may be used for a light sleep in polices or fire stations where a long-time deep sleep is not allowed.

REFERENCE SIGNS LIST

1: SLEEP DEPTH MAINTAINING DEVICE
2: SLEEP DEPTH DETERMINING DEVICE
3: MAINTENANCE CONTROL UNIT
4: SLEEP DEPTH DB
5: STIMULUS GIVING UNIT
6: SENSE DETECTING UNIT
7: SLEEP DEPTH DETERMINING UNIT
H, H1: AMPLITUDE
M: OBJECT PERSON
P1: FIRST STIMULUS
P2: SECOND STIMULUS
P3 to P8: MAINTENANCE STIMULUS
S1, S2, S3, S4: DEPTH OF SLEEP
T1, T2, T3, T4: SENSITIVITY THRESHOLD
T2a: FIRST STIMULUS INTENSITY
T2b: SECOND STIMULUS INTENSITY
W: BRAIN WAVE

The invention claimed is:

1. A sleep depth determining device for determining an object person's depth of sleep using a sensitivity threshold which is a minimum stimulus intensity that can be sensed by the object person in a sleep state with a predetermined depth of sleep and which maintains the object person's depth of sleep at an intermediate level lower than a maximum level, comprising:

a stimulus giving unit that gives the object person a first stimulus with a first stimulus intensity and a second stimulus with a second stimulus intensity greater than the first stimulus intensity;

a sense detecting unit that detects whether the object person senses the first stimulus and the second stimulus;

a sleep depth determining unit that determines that the object person's depth of sleep is a depth of sleep corresponding to a sensitivity threshold between the first stimulus intensity and the second stimulus intensity when the sense detecting unit detects that the object person does not sense the first stimulus but senses the second stimulus; and a maintenance control unit that determines a condition of a maintenance stimulus to be given to the object person on the basis of the sensitivity threshold in the depth of sleep of the intermediate level so as to maintain the object person's depth of sleep at the intermediate level and causes the stimulus giving unit to give the object person the maintenance stimulus on the basis of the determined condition, after the sleep depth determining unit determines that the object person's depth of sleep is the depth of sleep of the intermediate level.

2. The sleep depth determining device according to claim 1, wherein the depths of sleep and the sensitivity thresholds corresponding to the depths of sleep are set by stages in advance, and wherein the stimulus giving unit gives the object person a stimulus with a stimulus intensity smaller than a predetermined sensitivity threshold set in advance to correspond to a predetermined depth level of sleep as the first stimulus and gives the object person a stimulus with a stimulus intensity greater than the predetermined sensitivity threshold as the second stimulus.

3. The sleep depth maintaining device according to claim 1, wherein the maintenance control unit causes the sense detecting unit to detect whether the object person senses the maintenance stimulus when the maintenance stimulus is given to the object person, and adjusts the condition so as to increase a stimulus intensity of the maintenance stimulus when it is detected that the object person does not sense the maintenance stimulus.

4. The sleep depth maintaining device according to claim 3, further comprising a maintenance time calculating unit that calculates a maintenance time when the sense detecting unit detects that the object person senses the maintenance stimulus, wherein the maintenance control unit adjusts the condition so as to increase the stimulus intensity of the maintenance stimulus in reverse proportion to a length of the maintenance time at the time of raising the stimulus intensity of the maintenance stimulus.

5. The sleep depth maintaining device according to claim 3, further comprising a maintenance ratio calculating unit that calculates a maintenance ratio which is a ratio of the number of times when the sense detecting unit detects that the object person senses the maintenance stimulus to the number of times when the maintenance stimulus is given to the object person, wherein the maintenance control unit adjusts the condition so as to increase the stimulus intensity of the maintenance stimulus in reverse proportion to a magnitude of the maintenance ratio at the time of raising the stimulus intensity of the maintenance stimulus.

6. A sleep depth determining method of determining an object person's depth of sleep using a sensitivity threshold which is a minimum stimulus intensity that can be sensed by the object person in a sleep state with a predetermined depth of sleep and which maintains the object person's depth of sleep at an intermediate level lower than a maximum level, comprising:

a stimulus giving step of causing a stimulus giving unit to give the object person a first stimulus with a first stimulus intensity and a second stimulus with a second stimulus intensity greater than the first stimulus intensity;

a sense detecting step of causing a sense detecting unit to detect whether the object person senses the first stimulus and the second stimulus;

a sleep depth determining step of causing a sleep depth determining unit to determine that the object person's depth of sleep is a depth of sleep corresponding to a sensitivity threshold between the first stimulus intensity and the second stimulus intensity when it is detected in the sense detecting step that the object person does not sense the first stimulus but senses the second stimulus; and a maintenance stimulus giving step that uses a maintenance control unit to determine a condition of a maintenance stimulus to be given to the object person on the basis of the sensitivity threshold in the depth of sleep of the intermediate level so as to maintain the object person's depth of sleep at the intermediate level and causes the stimulus giving unit to give the object person the maintenance stimulus on the basis of the determined condition, after the sleep depth determining unit determines that the object person's depth of sleep is the depth of sleep of the intermediate level.

\* \* \* \* \*